(12) United States Patent
Murthy et al.

(10) Patent No.: US 7,615,647 B2
(45) Date of Patent: Nov. 10, 2009

(54) PROCESS FOR PRODUCING ATORVASTATIN HEMICALCIUM

(75) Inventors: K.S. Keshava Murthy, Ancaster (CA); Yajun Zhao, Brantford (CA); Daqing Che, Brantford (CA); Bhaskar Reddy Guntoori, Brantford (CA); Sammy Chris Duncan, Brantford (CA); Stephen E. Horne, Burlington (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 11/197,413

(22) Filed: Aug. 5, 2005

(65) Prior Publication Data

US 2006/0199855 A1 Sep. 7, 2006

(30) Foreign Application Priority Data

Mar. 1, 2005 (CA) .................................. 2499047

(51) Int. Cl.
*C07D 207/30* (2006.01)
(52) U.S. Cl. ............... 548/560; 514/423; 548/537; 548/561; 548/562; 548/563
(58) Field of Classification Search ............ 548/537, 548/560, 561, 562, 563; 514/423
See application file for complete search history.

(56) References Cited

U.S. PATENT DOCUMENTS

| | | | |
|---|---|---|---|
| 4,681,893 A | 7/1987 | Roth | |
| 5,003,080 A | 3/1991 | Butler et al. | |
| 5,273,995 A * | 12/1993 | Roth | 514/422 |
| 5,298,627 A | 3/1994 | Butler et al. | |
| 6,528,661 B2 * | 3/2003 | Niddam et al. | 548/537 |
| 6,583,295 B1 | 6/2003 | Pflaum | |
| 6,841,554 B2 * | 1/2005 | Taylor et al. | 514/275 |
| 2004/0220255 A1 | 11/2004 | van der Schaaf et al. | |

FOREIGN PATENT DOCUMENTS

| WO | WO-01/36384 A1 | 5/2001 |
|---|---|---|
| WO | WO-03/068739 A1 | 8/2003 |

OTHER PUBLICATIONS

John Landgrebe, Extraction and Drying, Chapter 6, Organic Laboratory, 4th edition, p. 123-132.*
Baumann. Kelvin L et al.; The Convergent Synthesis of CI-981. an Optically Active, Highly Potent Tissue Selective Inhibitor of HMG-CoA Reductase; Tetrahedron Letters; vol. 33. No. 17, pp. 2283-2284, 1992; Pergamon Press Ltd., Great Britain.

* cited by examiner

Primary Examiner—Young Chu
(74) Attorney, Agent, or Firm—Apotex Inc.

(57) ABSTRACT

A process is provided for preparing pharmaceutical grade atorvastatin hemicalcium salt comprising:
(a) deesterifying,

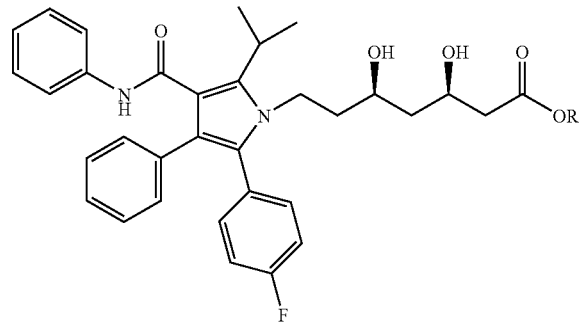

wherein R is an ester protecting group to

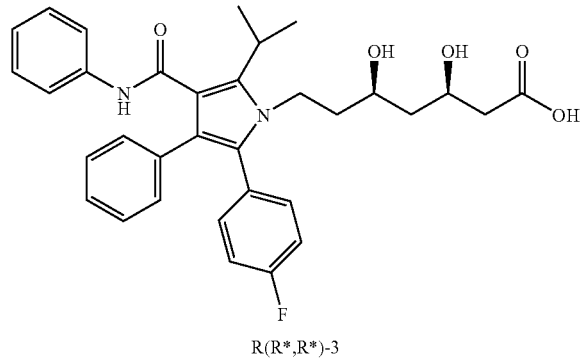

R(R*,R*)-3

(b) extracting R(R*,R*)-3 into an organic solvent or mixture of solvents,
(c) adding a base of formula $NR_1R_2R_3$ wherein $R_1$, $R_2$ and $R_3$ are independently selected from H, substituted or non-substituted C1 to C7 alkyl, C6 to C9 aryl, C8 to C10 aralkyl or aminoalkyl to form atorvastatin base salt,
(d) isolating by precipitation of the above atorvastatin base salt and purifying when necessary,
(e) converting atorvastatin base salt to atorvastatin hemicalcium salt by treatment with a calcium salt solution, and
(f) isolating the atorvastatin hemicalcium salt.

12 Claims, No Drawings

PROCESS FOR PRODUCING ATORVASTATIN HEMICALCIUM

FIELD OF INVENTION

This invention relates to the improved preparation and purification of intermediate atorvastatin base salt and useful in the preparation of highly pure atorvastatin hemicalcium including the amorphous form.

BACKGROUND OF THE INVENTION

Atorvastatin is a reductase inhibitor of the enzyme 3-hydroxy-3-methylglutarate-coenzyme A (HMG-CoA) and therefore is a useful anti-hyperlipoproteinemic agent. It has proven to be a highly effective medicament for the treatment of disorders such as hyperlipidemia and hypercholesterolemia which are conditions that are known risk factors for arteriosclerosis and coronary heart disease. Atorvastatin is chemically [R-(R*,R*)]-2-(4-fluorophenyl)-β,δ-dihydroxy-5-(1-methylethyl)-3-phenyl-4-(phenylcarbamoyl)-1H-pyrrole-1-heptanoic acid and is marketed as its calcium salt in a 2:1 molar ratio between the atorvastatin and the calcium (designated herein as atorvastatin hemicalcium salt) under the brand name Lipitor™.

DISCUSSION OF PRIOR ART

Several processes for the preparation of atorvastatin hemicalcium are reported. For instances U.S. Pat. No. 4,681,893 (U.S. '893) disclosed a process for making racemic trans-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-carboxamide, "the racemic atorvastatin lactone". The latter stage of the process is depicted in Scheme 1.

The lactone is prepared from the crude acid 3 by refluxing in toluene and further purified by chromatography and recrystallization in a mixture of toluene and ethyl acetate (example 1). Atorvastatin sodium salt 5 is then prepared by treating the lactone with sodium hydroxide (example 2).

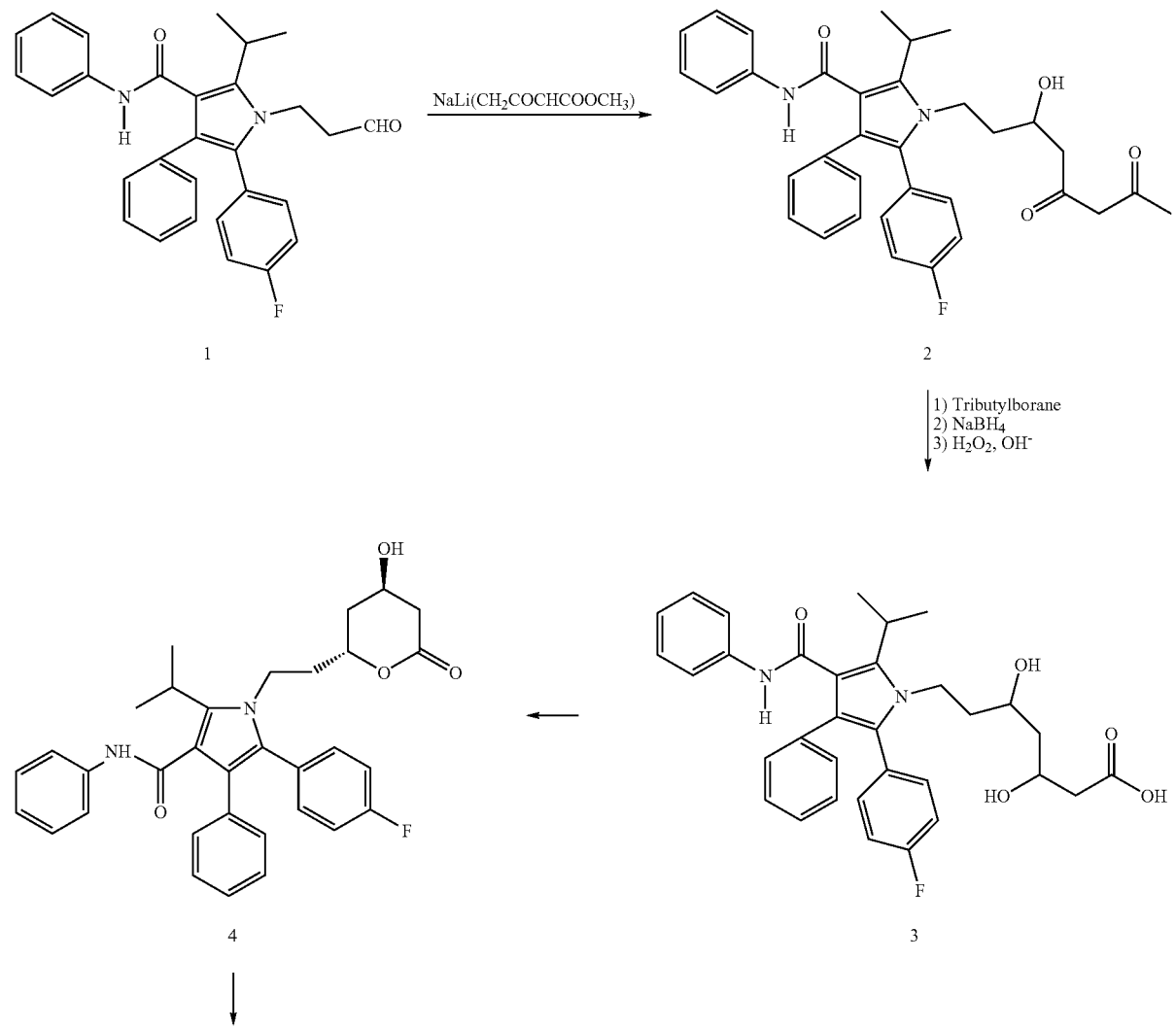

-continued

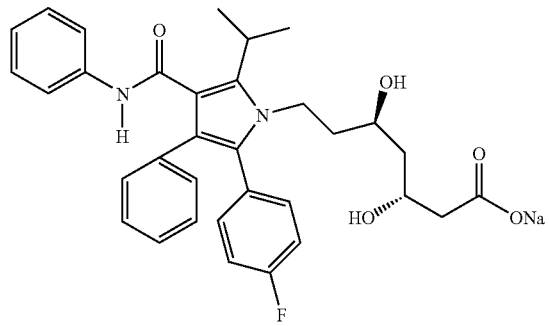

5

U.S. Pat. No. 5,273,995 (U.S. '995) teaches a route to enantiomeric Atorvastatin hemicalcium (9) as shown in Scheme 2. This route involves the alkylation of aldehyde 1 to form the chiral ester 6 followed by transesterification to the methylester 7 using sodium methoxide. Methylester 7 is then reacted with the lithium enolate of tert-butylacetate to form the β-ketoester 8, which is subsequently reduced by trialkylborane and hydrolyzed to form atorvastatin lactone (4). The sodium salt is prepared first by dissolving the lactone in methanol and water and adding a little less than one equivalent of sodium hydroxide to the solution until the lactone has been opened as determined by HPLC. The hemicalcium salt may be prepared from the sodium salt solution by treating with a half equivalent of calcium chloride dihydrate. U.S. '995 also describes the preparation and purification of the N-methylglucamine salt by first isolation by evaporation to dryness and then purification by recrystallization. However the use of the glucamine for the preparation of atorvastatin hemicalcium is not described. As well, the N-methylglucamine salt still contains 4% if N-methylglucamine in addition to residual acetone (0.67%) and water (0.4%).

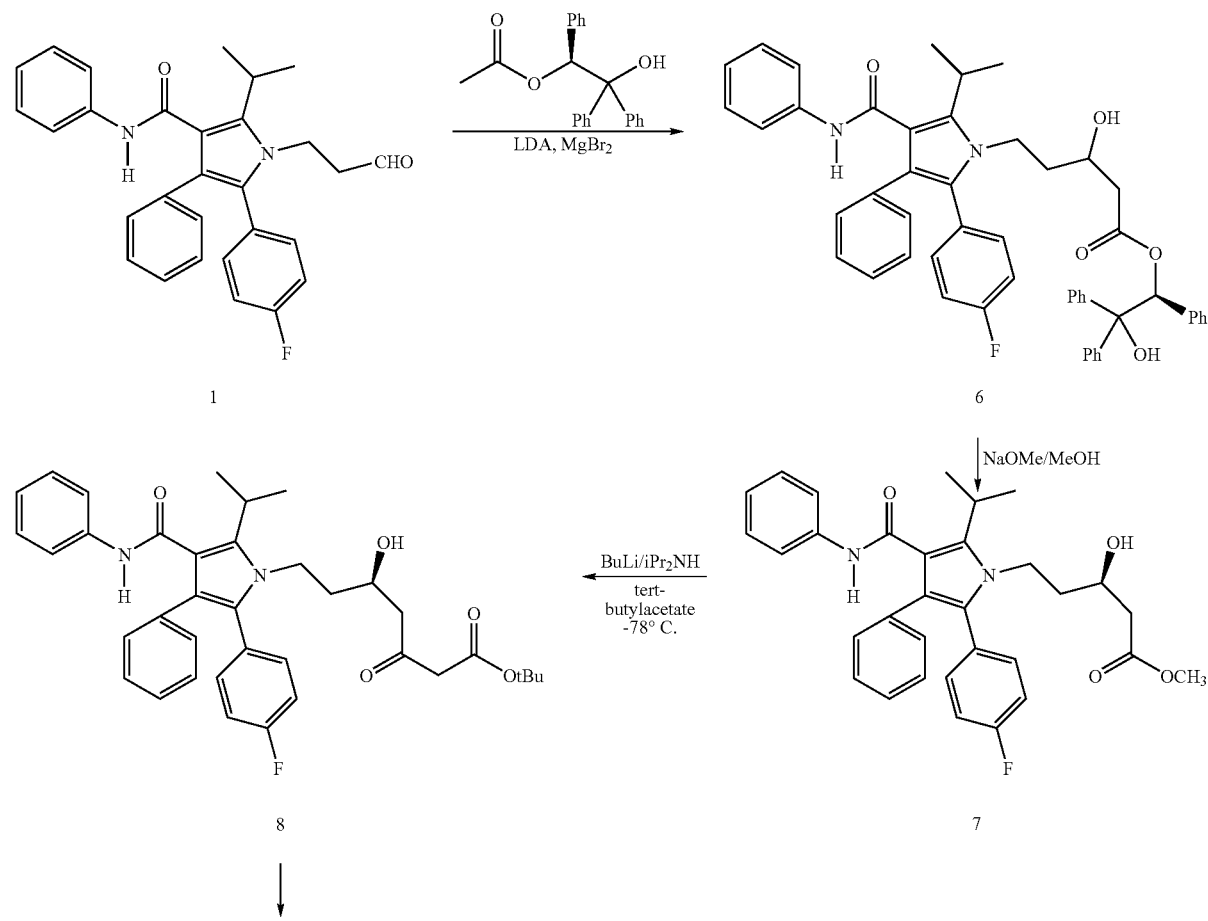

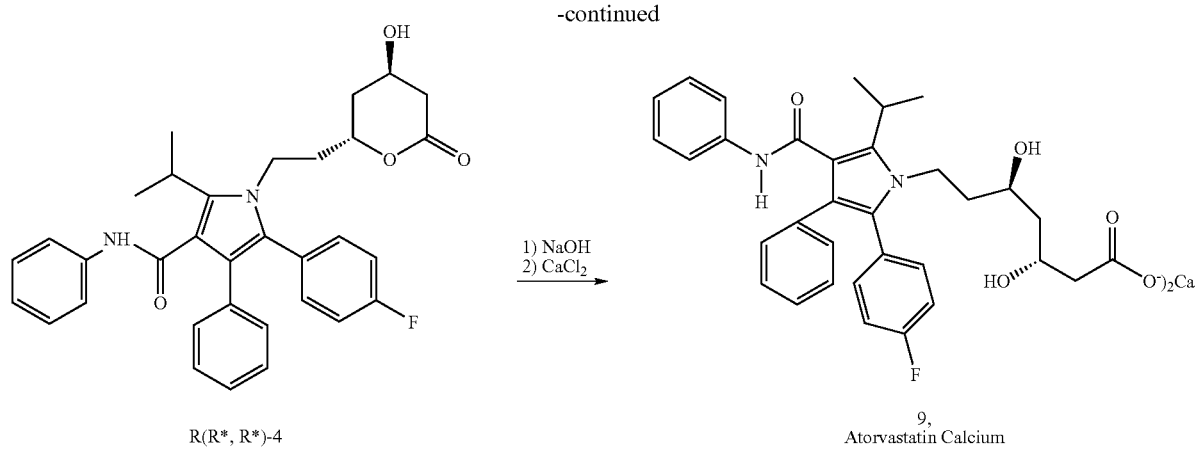
U.S. Pat. No. 5,003,080 (10a→12a) and U.S. Pat. No. 5,298,627 (10b→12b) teach two improved, more convergent processes for preparing atorvastatin in which the side chain bearing the β,δ-dihydroxy carboxylic acid derivatives are incorporated in a single step rather than being elaborated from a propanal side chain as described in U.S. '893 and U.S.'995. These routes are depicted in Scheme 3.
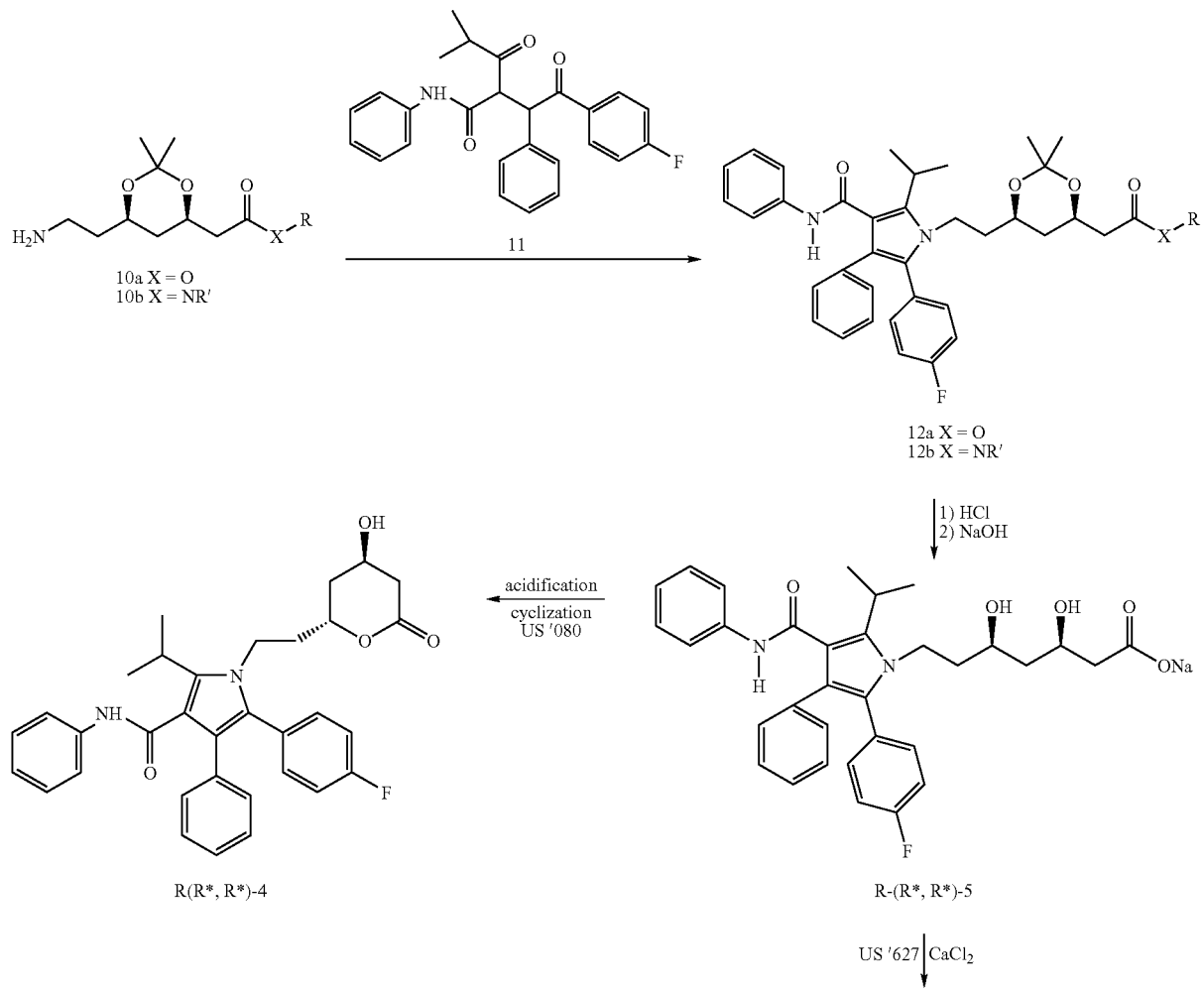

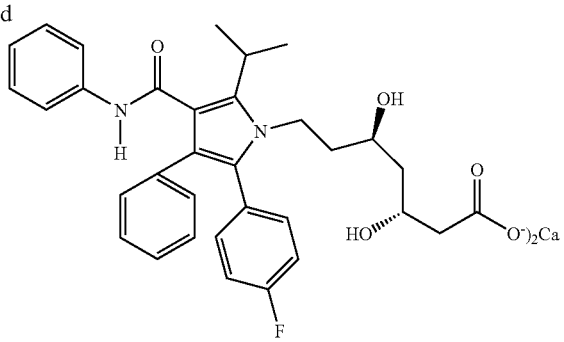

9,
Atorvastatin Calcium

The coupling step of the process is a Paal Knorr reaction to form the pyrrole. After the coupling step, the acetonide protecting group on the β and δ hydroxy is cleaved with acid, followed by basic hydrolysis of 12a (U.S. Pat. No. 5,003,080) and 12b (U.S. Pat. No. 5,298,627). The resulting sodium salt is then transferred to its hemicalcium salt without isolation and purification of any intermediate, or after acidification the lactone 4 is prepared as described in U.S. Pat. No. 5,003,080.

The preparation of atorvastatin hemicalcium salt in the above mentioned processes involves either the isolation and purification of lactone 4 or formation of the hemicalcium salt from the sodium salt directly without any isolation or purification of the intermediates. The first route (through lactone 4) has several disadvantages including the fact that it requires many steps and the lactonization generates impurities during the toluene reflux. Also, the purification step results in low yields. The second route (directly from sodium salt) suffers low purity of the finished product, which is especially problematic since the desired form of the finished product is amorphous atorvastatin hemicalcium. It is well known in the art that amorphous forms are difficult to purify for several reasons including the fact that the impurities can be trapped within the glass-like structure and that purification often induces crystallinity.

To overcome the above deficiency U.S. Pat. No. 6,528,661 teaches an improved process whereby the diol ester 14 is hydrolyzed under basic conditions (calcium hydroxide) without going though the sodium salt as shown in Scheme 4. Though this process does improve the overall efficiency, the impurities generated during the de-protection steps cannot be removed because the intermediates are not isolated or purified.

Scheme 4

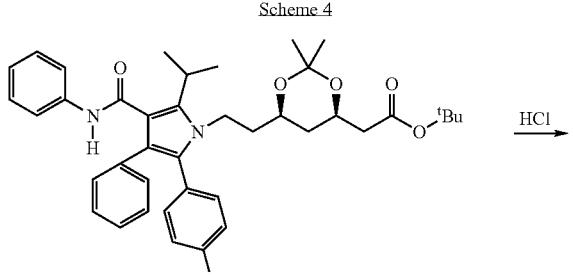

13

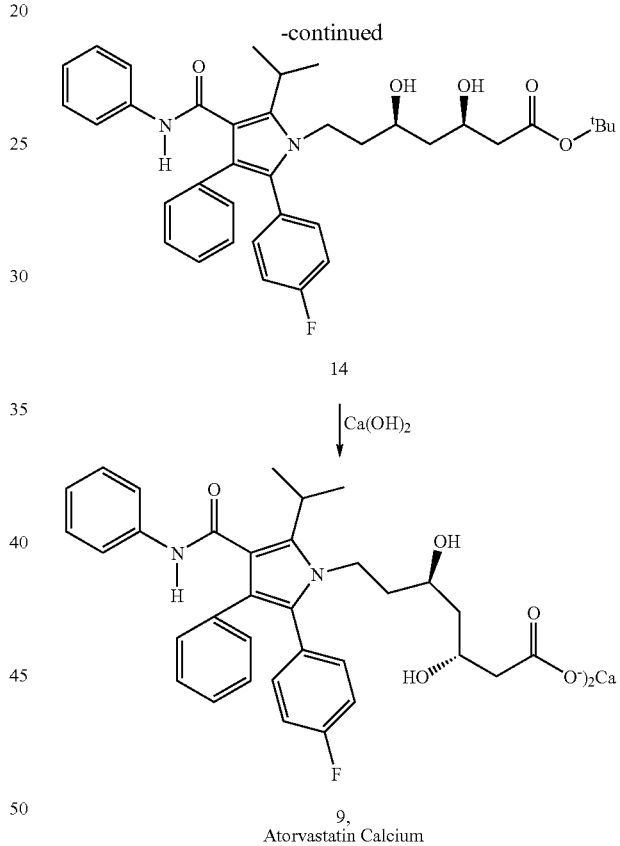

14

↓ Ca(OH)$_2$

9,
Atorvastatin Calcium

U.S. '995 teaches that atorvastatin may form a salt with alkali metal, ammonia and other amines. According to U.S. '995, atorvastatin hemicalcium salt may be manufactured by treating atorvastatin salt with calcium chloride. However, atorvastatin sodium salt is difficult to isolate and purify because of its poor filterability.

Another attempt to prepare atorvastatin salt is disclosed in US 2004/220255. Therein the atorvastatin free acid R(R*, R*)-3 is dissolved in ethanol and ammonia is added and the salt is obtained by evaporating the solvent to a colorless or slightly beige foam. This process is not expected to remove impurities contained in the free acid R(R*,R*)-3. In one example, this foam is then converted into atorvastatin hemicalcium as crystalline form A.

WO 03/068739 describes a method for the manufacture of amorphous atorvastatin hemicalcium using an aqueous extractive technique wherein atorvastatin acid is converted into a $M^+$ or ammonium cation of formula $R_nN^+H_{(4-n)}$ and typically without isolating the intermediate, it is converted into atorvastatin hemicalcium or another salt or atorvastatin lactone. In one example, the triethylammonium salt was isolated by evaporation to dryness; however this again would not offer any improvement in the purity of the compound.

WO 01/36384 describes a method for the preparation of a purportedly new atorvastatin calcium form, designated as Form V, by taking atorvastatin into a solvent and forming a metal, ammonium or alkyl, aryl or alkaryl ammonium salt solution and, without isolation, converting it into atorvastatin hemicalcium Form V or hydrates thereof. There are no examples given for the organic solvent soluble ammonium or alkyl, aryl or alkaryl ammonium salt solution.

It is therefore an object of this invention to provide an improved process for the manufacture of atorvastatin hemicalcium relative to the prior art processes without the problems associated therewith. Further and other objects of the invention will be realized by those skilled in the art from the following Summary of Invention and Description of Embodiments.

SUMMARY OF THE INVENTION

Surprisingly and unexpectedly it was found that highly pure (pharmaceutical grade) atorvastatin hemicalcium can be prepared from purified atorvastatin ammonium or organic ammonium salts which have been isolated by precipitation. These salts are produced when atorvastatin acid is treated with ammonia or other organic amines in certain organic solvents and were conveniently isolated using a novel procedure. Amorphous or crystalline, more preferably amorphous, atorvastatin hemicalcium salt can be then formed by treating these salts with selected aqueous calcium salts.

As depicted in Scheme 5, the diol ester 15 wherein R is an ester protecting group, preferably a tert-butyl group, is the preferable starting material for this exemplary process. It can be isolated or obtained from other synthetic routes. The deesterification process can be achieved by, for example, base hydrolysis. The deesterified product can then be acidified, if required, to form the free carboxylic acid R(R*,R*)-3 which is extracted into an organic solvent. The preferred organic solvents can be dialkyl ethers such as methyl tert-butyl ether and diisopropyl ether; ketones such as methyl isobutyl ketone; and hydrocarbons such as toluene. A base of the formula $NR_1R_2R_3$, wherein $R_1$, $R_2$ and $R_3$ are independently selected from H, substituted or non-substituted C1 to C7 alkyl, C6 to C9 aryl, C8 to C10 aralkyl or aminoalkyl, is then added. Most preferably, the base is ammonia ($R_1$, $R_2$, $R_3$=H). Other preferred bases include methylamine, dimethylamine, trimethylamine, ethylenediamine, diisopropylamine, dicyclohexylamine, (S)- and (R)-methylbenzylamine. The base is added at preferably a low to elevated temperature, preferably at room temperature, and the atorvastatin base salt thus formed is isolated by, for example, by precipitation and filtration. Optionally, if desired, the atorvastatin base salt can be purified by trituration or recrystallization in a suitable organic solvent or solvent mixture. Both aqueous or neat solutions of the base can be used in the above processes. For the preparation of the ammonium salt ($R_1$, $R_2$, $R_3$=H), an aqueous ammonia solution is preferred. The atorvastatin base salt can be used in the next step after drying or without drying, preferably without drying. Optionally, if desired, the above atorvastatin base salts can be purified by trituration or re-crystallizing in a selected organic solvent or solvent mixture. For example, the salts of atorvastatin free acid R(R*,R*)-3 and diisopropylamine or dicyclohexylamine can be re-crystallized from organic solvent such as methyl tert-butyl ether and methyl tert-butyl ether, methanol mixture.

The atorvastatin base salts prepared by this process typically have purities of greater than 99% and the overall yield from 15 is more than 95%. This is superior to the prior art.

Atorvastatin hemicalcium salt can be prepared from the above isolated and purified, if required, atorvastatin ammonium and organic ammonium salts by dissolution in a water miscible organic solvent with or without water, followed by addition to an aqueous calcium salt solution such as calcium chloride or calcium acetate at preferably low to elevated temperature, preferably at room temperature. The formed atorvastatin hemi-calcium is isolated by filtration in near quantitative yield and having essentially the same purity as atorvastatin ammonium and organic ammonium salt.

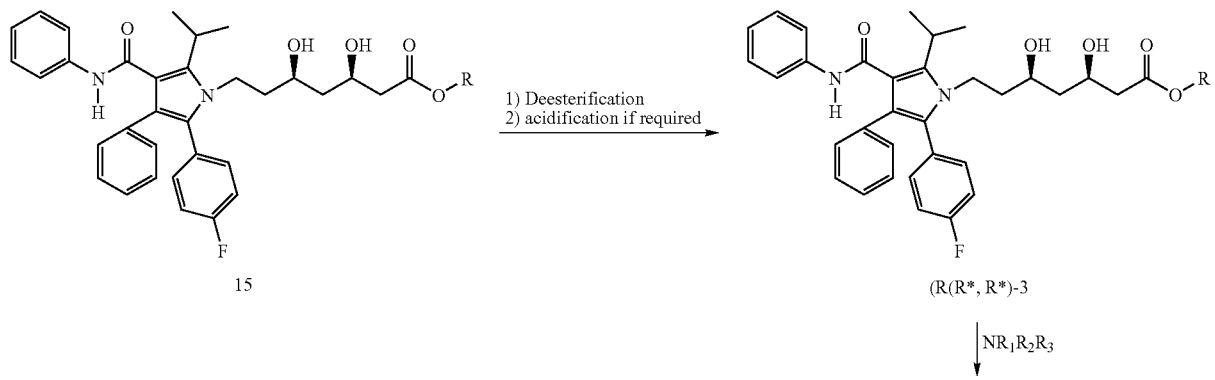

Scheme 5

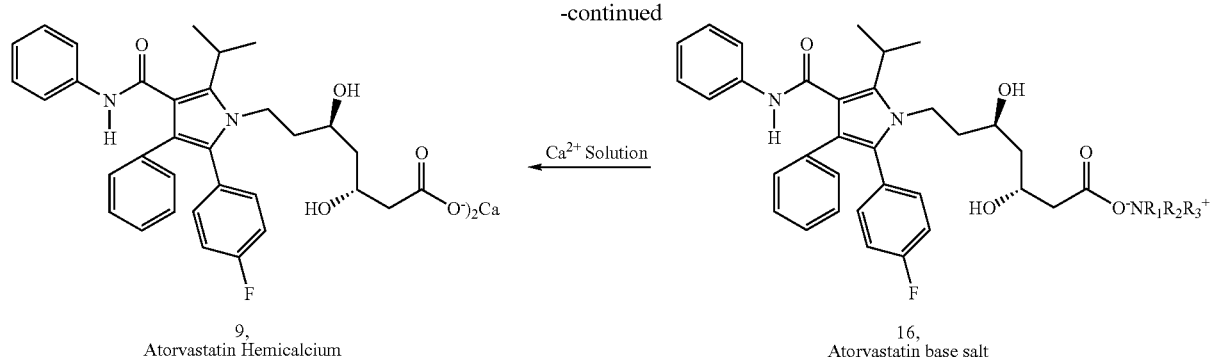

9,
Atorvastatin Hemicalcium

16,
Atorvastatin base salt

In another embodiment of the invention depicted in Scheme 6, if desired atorvastatin lactone (R(R*,R*)-4 can be conveniently prepared from an atorvastatin base salt by heating the purified base salt in an organic solvent, preferably toluene, and after cooling, isolation by filtration. The atorvastatin lactone can then be converted to atorvastatin hemicalcium by known methods.

Scheme 6

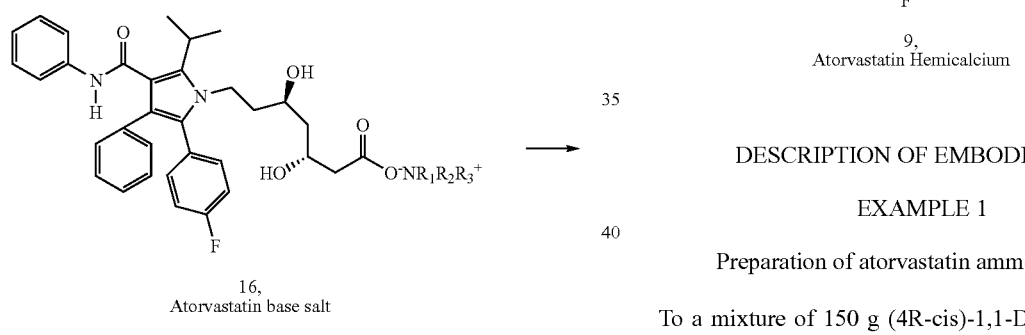

16,
Atorvastatin base salt

9,
Atorvastatin Hemicalcium

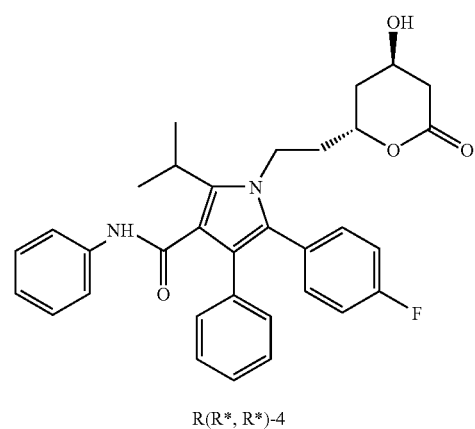

R(R*, R*)-4

DESCRIPTION OF EMBODIMENTS

EXAMPLE 1

Preparation of atorvastatin ammonium Salt

To a mixture of 150 g (4R-cis)-1,1-Dimethylethyl-6-{2-[[2-(4-fluorophenyl)]-5-(1-methylethyl)-3-phenyl-4-[(phenylamino)carbonyl]-1H-pyrrole-1-yl]ethyl}-2,2-dimethyl-1,3-dioxane-4-acetate 13 and 1.5 L MeOH was added 229 mL 1N aq. HCl solution. The mixture was warmed to about 50° C. and maintained for about 10 h before it was cooled to room temperature. 1 N NaOH solution (458 mL) was added and the mixture was warmed to about 60° C. for about 10 h. After cooling to room temperature the reaction mixture was acidified with diluted aqueous HCl solution and extracted three times with 300 mL portion of methyl tert-butyl ether. The combined organic layers were washed with brine and treated with 25.5 ml concentrated aqueous ammonia solution. The mixture was stirred for about 3 h and filtered, the damp cake was washed with methyl tert-butyl ether and used directly in the next step without drying.

Yield: 95% from 13.

HPLC purity: 99.25%.

A small sample was dried and characterized as following:

NMR (300 MHz, DMSO-$d_6$): δ(ppm)=7.51 (d, 2H); 7.29-7.16 (m, 6H); 7.12-7.05 (m, 4H); 7.05-6.95 (m, 2H); 6.40 (s, 1H); 4.01-3.87 (m, 1H); 3.82-3.70 (m, 2H); 3.58-3.48 (m, 1H); 3.30-3.16 (m, 1H); 2.20-1.97 (m, 2H); 1.69-1.47 (m, 2H); 1.46-1.32 (m, 7H); 1.31-1.20 (m, 1H).

IR (Nujol, cm$^{-1}$): 3272; 2923; 2853; 1648; 1597; 1528; 1509; 1461; 1377; 1316; 1222; 1157; 1110; 1075; 843; 750; 700.

EXAMPLE 2

Preparation of atorvastatin hemicalcium Salt from atorvastatin ammonium Salt

Atorvastatin ammonium salt (30 g, corrected for solvent and water) obtained from example 1 was dissolved in 30 mL THF and 250 mL water. The above solution was added to a solution of 5 g Ca(OAc)$_2$ monohydrate in 60 mL water. The mixture was stirred for 12 h and the solid was filtered. After washing with water the solid was dried and 27 g of atorvastatin hemicalcium salt was obtained.

HPLC purity: 99.18%

Water content by KF: 0.46%

The material obtained was characterized as amorphous form by means of DSC and PXRD analysis.

EXAMPLE 3

Preparation of (3R,5R)-1,1-Dimethylethyl-7-{2-(4-Fluorophenyl)-5-(1-methylethyl)-3-phenyl-4-[(phenylamino)carbonyl]-1H-pyrrole-1-yl}-3,5-dihydroxy-1-heptanoate 14

To the suspension of 20 g (4R-cis)-1,1-Dimethylethyl-6-{2-[[2-(4-flurophenyl)]-5-(1-methylethyl)-3-phenyl-4-[(phenylamino)carbonyl]-1H-Pyrrole-1-yl]ethyl}-2,2-dimethyl-1,3-dioxane-4-actate 13 in 200 mL methanol was added 30 mL 1N HCl dropwise. The resulting mixture is heated at about 35° C. for 3 h and then cooled down to room temperature. The solid was filtered and washed with water. After filtering and drying 14 g white powder was obtained.

$^1$H-NMR(300 MHz, CDCl$_3$): δ(ppm)=7.21-7.13 (m, 9H); 7.06 (d, 2H); 7.02-6.95 (m, 3H); 6.87 (s, 1H); 4.17-4.07 (m, 2H); 3.97-3.88 (m, 1H); 3.79-3.69 (m, 3H); 3.63-3.53 (m, 1H); 2.32 (d, 2H); 1.74-1.57 (m, 2H); 1.54 (d, 6H); 1.49-1.42 (m, 10H); 1.25 (d, 1H).

EXAMPLE 4

Preparation of atorvastatin ammonium Salt from (3R,5R)-1,1-Dimethylethyl-7-{2-(4-Fluorophenyl)-5-(1-methylethyl)-3-phenyl-4-[(phenylamino)carbonyl]-1H-pyrrole-1-yl}-3,5-dihydroxy-1-heptanoate 14

To the suspension of 6.14 g (3R,5R)-1,1-Dimethylethyl-7-{2-(4-Flurophenyl)-5-(1-methylethyl)-3-phenyl-4-[(phenylamino)carbonyl]-1H-Pyrrole-1-yl}-3,5-dihydroxy-1-hepatanoate 14 in MeOH (60 mL) was added a solution of 1N NaOH. The mixture is heated at about 55° C. for about 2.5 h and MeOH was removed under vacuum. After cooling to room temperature the reaction mixture is diluted with MTBE and acidified with dilute aqueous HCl. The separated organic layer is washed with water and treated with 1.5 equivalent aqueous Ammonia. The mixture was stirred for 2-3 h, filtered and washed with methyl tert-butyl ether. The damp cake can be used for next step without drying.

EXAMPLE 5

General Procedure of Preparation of atorvastatin Salt with Organic amines

To a mixture of 30 g (4R-cis)-1,1-Dimethylethyl-6-{2-[[2-(4-fluorophenyl)]-5-(1-methylethyl)-3-phenyl-4-[(phenylamino)carbonyl]-1H-pyrrole-1-yl]ethyl}-2,2-dimethyl-1,3-dioxane-4-acetate 13 and 500 mL MeOH was added 76.3 mL 1N aq. HCl solution. The mixture was warmed to about 50° C. and maintained for about 10 h before it was cooled to room temperature. 1 N NaOH solution (153 mL) was added and the mixture was warmed to about 60° C. for about 10 h. After cooling to room temperature the reaction mixture was acidified with diluted aqueous HCl solution and extracted three times with 100 mL portion methyl tert-butyl ether. The combined organic layers were washed with brine and treated with 1.2 eq amine. The mixture was stirred for about 3 h and filtered, the damp cake was washed with methyl tert-butyl ether and dried. The salt can also be used directly for the preparation of atorvastatin hemicalcium without drying.

5a: atorvastatin methylamine salt yield: 94%.

$^1$H-NMR(300 MHz, CDCl$_3$): δ(ppm)=7.26-6.91 (m, 14H); 6.15 (s, 3H); 4.18-3.85 (m, 3H); 3.67-3.46 (m, 2H); 2.41 (s, 3H); 2.30-2.19 (m, 1H); 2.17-2.02 (m, 1H); 1.73-1.34 (m, 9H); 1.28-1.17 (d, 1H).

5b: atorvastatin dimethylamine salt yield: 95%.

$^1$H-NMR(300 MHz, CDCl$_3$): δ(ppm)=7.25-6.88 (m, 14H); 6.20 (s, 2H); 4.18-3.86 (m, 3H); 3.77-3.66 (m, 1H); 3.62-3.48 (m, 1H); 2.58 (s, 6H); 2.36-2.14 (m, 2H); 1.76-1.35 (m, 9H); 1.28-1.17 (m, 1H).

5c: atorvastatin trimethylamine salt yield: 91%.

$^1$H-NMR(300 MHz, CDCl$_3$): δ(ppm)=7.25-6.88 (m, 14H); 6.20 (s, 1H); 4.19-4.02 (m, 2H); 3.99-3.86 (m, 1H); 3.82-3.69 (m, 1H); 3.64-3.48 (m, 1H); 2.70 (s, 9H); 2.41-2.19 (m, 2H); 1.80-1.38 (m, 9H); 1.25 (d, 2H).

5d: atorvastatin ethylenediamine salt yield: 95%.

$^1$H-NMR(300 MHz, CDCl$_3$): δ(ppm)=7.24-6.88 (m, 14H); 4.17-3.82 (m, 3H); 3.66-3.11 (m, 6H); 2.90 (s, 4H); 2.31-2.06 (m, 2H); 1.73-1.35 (m, 9H); 1.23-1.17 (m, 1H).

5e: atorvastatin diisopropylamine salt yield: 95%.

$^1$H-NMR(300 MHz, CDCl$_3$): δ(ppm)=7.24-6.85 (m, 14H); 4.19-3.86 (m, 3H); 3.68-3.52 (m, 1H); 3.35-3.19 (m, 2H); 2.32-2.09 (m, 2H); 1.79-1.18 (m, 22H).

5f: atorvastatin dicyclohexylamine salt yield: 95%.

$^1$H-NMR(300 MHz, CDCl$_3$): δ(ppm)=7.24-6.85 (m, 14H); 4.22-3.87 (m, 3H); 3.82-3.72 (m, 1H); 3.68-3.52 (m, 1H); 2.98-2.85 (m, 2H); 2.33-2.08 (m, 2H); 2.07-1.05 (m, 30H).

5g: atorvastatin (S)-methylbenzylamine salt yield: 88%

$^1$H-NMR(300 MHz, CDCl$_3$): δ(ppm)=7.36-6.88 (m, 19H); 4.22-4.05 (m, 2H); 3.99-3.76 (m, 2H); 3.67-3.50 (m, 2H); 2.03-1.80 (m, 2H); 1.77-1.44 (m, 11H); 1.39-1.23 (m, 1H); 1.07 (d, 1H).

EXAMPLE 6

Preparation of atorvastatin ammonium Salt from atorvastatin diisopropylamine Salt A suspension of 50 g atorvastatin diisopropylamine salt in 600 mL methyl tert-butyl ether and 300 mL water was cooled to 0-10° C. 10 g concentrated aqueous HCl solution was added and the mixture was stirred for about 1 h. The organic layer was separated and washed with 300 mL brine. The organic layer was cooled to 0-10° C. and added 7.5 ml concentrated aqueous ammonia solution. After stirring for about 3 h the solid was filtered and washed with methyl tert-butyl ether. The damp cake can be used for next step without drying.

EXAMPLE 7

Preparation of atorvastatin ammonium Salt from atorvastatin dicyclohexylamine Salt A suspension of 100 g atorvastatin dicyclohexylamine salt in 1.2 L methyl tert-butyl ether and 600 mL water was cooled to 0-10° C. 25 g concentrated aqueous HCl solution was added and the mixture was stirred for about 1 h. The mixture was filtered and from the filtrate the organic layer was separated and washed with 600 mL brine. The organic layer was cooled to 0-10° C. and added 15 ml concentrated aqueous ammonia solution. After stirring for about 3 h the solid was filtered and washed with methyl tert-butyl ether. The damp cake can be used for next step without drying.

EXAMPLE 8

Preparation of atorvastatin ammonium Salt from atorvastatin hemicalcium Salt A suspension of 100 g atorvastatin hemicalcium salt in 1.2 L methyl tert-butyl ether and 600 mL water was cooled to 0-10° C. 20 g concentrated aqueous HCl solution was added and the mixture was stirred for about 1 h. The organic layer was separated and washed with 500 mL brine. The organic layer was cooled to 0-10° C. and added 15 ml concentrated aqueous ammonia solution. After stirring for about 3 h the solid was filtered and washed with methyl tert-butyl ether. The damp cake can be used for next step without drying.

EXAMPLE 9

Preparation of atorvastatin lactone from atorvastatin ammonium Salt 5.75 g atorvastatin ammonium salt was suspended in 60 mL toluene and the mixture was heated under reflux for 12 h. After cooling to room temperature the solid was filtered and washed with toluene. After drying under vacuum 3.83 g atorvastatin lactone was obtained as off-white solid.

EXAMPLE 10

Preparation of atorvastatin hemicalcium Salt from atorvastatin diisopropyl amine Salt Atorvastatin diisopropylamine salt (4 g) was dissolved in 10 mL THF and 25 mL water. The above solution was added to a solution of 1 g Ca(OAc)$_2$ monohydrate in 22 mL water. The mixture was stirred for 6 h and the solid was filtered. After wash with water the solid was dried and 2.9 g of atorvastatin hemicalcium salt was obtained.

EXAMPLE 11

Purification of atorvastatin diisopropylamine Salt

A mixture of 10 g atorvastatin diisopropyl amine salt obtained from example 5 and 60 mL methyl tert-butyl ether and 20 mL methanol was refluxed for 12 h. The mixture was cooled to room temperature and the solid was filtered and washed with methyl tert-butyl ether and methanol mixture (3:1). After drying 8.8 g pure atorvastatin diisopropylamine salt was obtained.

While the foregoing provides a detailed description of preferred embodiments of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

What is claimed is:

1. A process for preparing atorvastatin hemicalcium salt wherein the purity is more than 99% comprising:

(a) deesterifying,

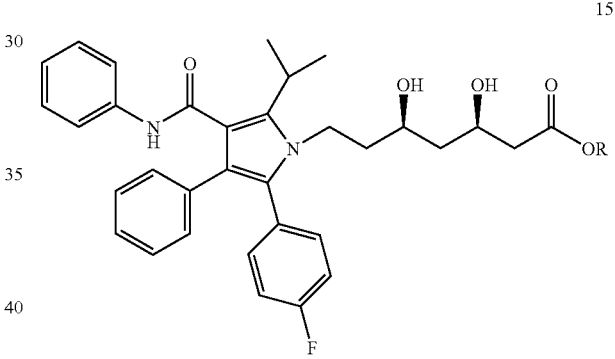

wherein R is an ester protecting group to

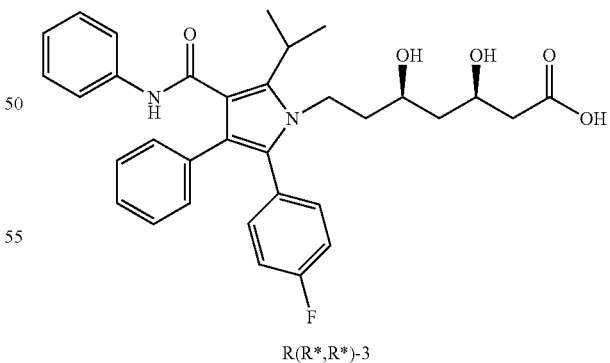

R(R*,R*)-3

(b) extracting R(R*,R*)-3 into an organic solvent or mixture of solvents, (c) adding a base of formula NR$_1$R$_2$R$_3$ wherein R$_1$, R$_2$ and R$_3$ are independently selected from H, substituted or non-substituted C1 to C7 alkyl, C6 to C9 aryl, C8 to C10 aralkyl or aminoalkyl to form atorvastatin base salt, (d) isolating by precipitation of the above atorvastatin base salt and purifying when necessary,
(e) converting atorvastatin base salt to atorvastatin hemicalcium salt by treatment with a calcium salt solution, and
(f) isolating the atorvastatin hemicalcium salt.

2. A process according to claim 1 wherein R is tert-butyl.

3. A process according to claim 2 wherein step a is accomplished by base hydrolysis.

4. A process according to claim 1 wherein R1, R2 and R3 are each hydrogen.

5. The process according to any one of claims 1 and 3 wherein the extraction step for R(R*,R*)-3 (step b) is a C4 to C8 dialkyl ether, a C4 to C8 dialkyl ketone, a C4 to C8 dialkyl ester, a C6 to C9 aromatic hydrocarbon of a C7 to C10 aralkyl hydrocarbon.

6. The process according to any one of claims 1 and 3 wherein the extraction step for R(R*,R*)-3 is methyl isobutyl ketone.

7. The process according to any one of claims 1 and 3 wherein the extraction step for R(R*,R*)-3 is methyl tert-butyl ether.

8. The process according to any one of claims 1 and 3 wherein atorvastatin base is converted to atorvastatin hemicalcium by treatment with an aqueous calcium chloride or calcium acetate solution.

9. The process according to claim 2 wherein the extraction step for R(R*,R*)-3 (step b) is a C4 to C8 dialkyl ether, a C4 to C8 dialkyl ketone, a C4 to C8 dialkyl ester, a C6 to C9 aromatic hydrocarbon of a C7 to C10 aralkyl hydrocarbon.

10. The process according to claim 2 wherein the extraction step for R(R*,R*)-3 is methyl isobutyl ketone.

11. The process according to claim 2 wherein the extraction step for R(R*R*)-3 is methyl tert-butyl ether.

12. The process according to claim 2 wherein atorvastatin base is convened to atorvastatin hemicalcium by treatment with an aqueous calcium chloride or calcium acetate solution.

* * * * *